United States Patent [19]

Segal

[11] Patent Number: 5,624,451
[45] Date of Patent: Apr. 29, 1997

[54] FLEXIBLE BLADE FOR REMOVING SKIN LESIONS

[75] Inventor: Robert J. Segal, Quincy, Ill.

[73] Assignee: American Safety Razor, Verona, Va.

[21] Appl. No.: 319,054

[22] Filed: Oct. 6, 1994

Related U.S. Application Data

[63] Continuation of Ser. No. 137,727, Oct. 18, 1993, abandoned.

[51] Int. Cl.$^6$ ............................................ A61B 17/32
[52] U.S. Cl. ........................ 606/131; 606/167; 30/346.5
[58] Field of Search ......................... 606/131, 132, 606/167; 30/49, 346.5, 346.55, 346.61, 32, 47, 48, 50, 353

[56] References Cited

U.S. PATENT DOCUMENTS

| | | |
|---|---|---|
| 951,456 | 3/1910 | Saxton . |
| 1,174,932 | 3/1916 | Grenier . |
| 1,893,524 | 1/1933 | Shanley . |
| 1,934,151 | 11/1933 | Slama et al. . |
| 1,974,568 | 9/1934 | Grotenhuis . |
| 2,035,110 | 3/1936 | Becker et al. . |
| 2,041,778 | 5/1936 | Peters ................................. 30/93 |
| 2,361,921 | 11/1944 | Albert . |
| 2,453,198 | 11/1948 | Corbett ............................... 30/169 |
| 2,983,045 | 5/1961 | Diatikar, Jr. ...................... 30/346.61 |
| 3,583,403 | 6/1971 | Pohl et al. . |
| 3,688,407 | 9/1972 | Paquette . |
| 3,916,418 | 10/1975 | Neveu . |
| 3,961,418 | 6/1976 | Neveu ................................. 30/123.5 |
| 4,038,986 | 8/1977 | Mahler ................................. 606/132 |
| 4,221,222 | 9/1980 | Detsch ................................. 606/132 |
| 4,438,767 | 3/1984 | Nelson ................................. 606/131 |
| 4,516,320 | 5/1985 | Peleckis . |
| 4,542,742 | 9/1985 | Winkelman ......................... 606/167 |
| 4,651,734 | 3/1987 | Doss et al. . |
| 4,690,139 | 9/1987 | Rosenburg . |
| 4,782,590 | 11/1988 | Pope . |
| 4,887,356 | 12/1989 | Rudd, Sr. . |
| 4,893,641 | 1/1990 | Strickland .......................... 606/131 |
| 4,912,846 | 4/1990 | Yu ....................................... 30/346.55 |
| 4,916,816 | 4/1990 | Richman ............................. 30/49 |
| 4,943,295 | 7/1990 | Hartlaub et al. ................... 606/131 |
| 5,116,346 | 5/1992 | Yeh ..................................... 606/131 |
| 5,555,892 | 9/1996 | Tipton ................................ 128/757 |

OTHER PUBLICATIONS

DermQuest–"Introducing a Revolutionary New Biopsy Shaver" Brochure, Tampa, Florida (Jul. 1994).

Primary Examiner—Michael Powell Buiz
Assistant Examiner—Patrick W. Rasche
Attorney, Agent, or Firm—McDermott, Will & Emery

[57] ABSTRACT

A digitally flexible surgical blade suitable for tangential excision of skin lesions and unusual skin colorations wherein the blade comprises a flexible, one-piece, flat body having lobes projecting frontally from the body to shield the user's fingers from contact with the blade's cutting edge. The blade ends provide safe and efficient finger grips and the cutting edge does not extend along the full length of the blade's leading edge but only between the projecting lobes.

14 Claims, 2 Drawing Sheets

FLEXIBLE BLADE FOR REMOVING SKIN LESIONS

This is a continuation application of application Ser. No. 08/137,727 filed Oct. 18, 1993 now abandoned.

BACKGROUND OF THE INVENTION

Surgical excision of flat and protuberant skin lesions may involve cutting through the dermis about the periphory of the lesion with a stiff bladed scapel or other keen-edged tool held generally perpendicularly to the skin surface. Such deep incision of skin tissue produces bleeding and usually requires suture closure to induce primary intention healing of the wound. If such full-thickness dermal incision is not required to remove the lesion, an alternate, somewhat less traumatic, procedure involves tangential excision or horizontal slicing of skin tissue without cutting through the dermis whereby bleeding is avoided, or at least greatly reduced, and secondary intention healing of the wound can be expected.

Transverse or tangential excision of various skin lesions is commonly performed by dermatologists using an unaltered double-edged razor blade. The user typically places his thumb and index finger upon opposite end surfaces of the blade and squeezes the ends toward one another causing the blade to bow convexly away from the finger tips into a U-shape. With the blade gripped and compressed in this manner, it may be positioned at or near the periphory of a lesion; and, thereafter, the arcuate bottom of the blade is advanced relative to the lesion with a scooping or slicing action. The cutting technic employed by the user will vary depending on such considerations as the size, shape and type of lesion encountered and depending on the purpose of the procedure.

While the utilization of commercially available double-edged razor blades as a simple and effective means to accomplish tangential excisions is well known and widely employed by dermatologists, users recognize certain undesirable aspects of this practice. Principal among these is the risk of accidentally cutting fingers on the sharpened longitudinal edges of a blade. Obviously this risk is present as the blade is handled in preparing it for use, as for example, in cleaning it of the usual rust-inhibiting lubricant and in sterilizing the same. When the user grips the blade between his thumb and index finger, a marginal end of a sharpened edge may come into engagemant with the user's gloved finger or thumb; and, subsequent compression of the blade ends necessary to effect bowing of the blade body may cause this sharp surface to puncture the glove and pierce the skin. Such risk of accidental contact with the sharpened blade edges is especially great where the user's fingers are large and when the required squeezing force applied by the fingers is substantial.

As shown in FIGS. 2(a)–(d) of the drawings of prior art devices, the extremely thin end surfaces of the blade typically have intersecting edges forming corners which can penetrate both a surgical glove and subjacent skin unless the user has developed the skill to maintain a steady grasp of the blade while limiting the digital pressure on the blade ends to only the minimum required for correct blade flexing. This danger is exacerbated by the common practice among dermatologists of breaking a standard blade in half along its longitudinal centerline thereby increasing the flexibility of the surgical tool and also salvaging the unused blade edge for future use. The drawing presented herein of a prior art blade so broken clearly indicates that the broken ends include dangerously jagged surfaces to which the user's fingers are unavoidably exposed due to the drastic reduction in the extent of the gripping surfaces along the blade ends. Clearly an additional hazard is presented to an individual who undertakes to break a thin steel razor blade without appropriate safeguards.

From the foregoing it will be appreciated that the adaptation of a flexible razor blade as a surgical implement is dangerous to the user largely because a razor blade comprises a cutting tool which was never intended to be digitally grasped and manipulated. To the contrary, skin-incising devices such as scapels, scissors and dermatomes, for example, are provided with suitable handles or grips which position and help to maintain the user's hand and fingers some distance from dangerously sharp edges.

It is believed that, in order to fulfill the needs of professionals wishing to tangentially excise skin lesions, a special blade for this purpose should have these characteristics:

1. The cutting edge should be easily flexed by digital compression of the blade.
2. The blade-gripping digits of the user should be adequately protected from inadvertent contact with all sharp blade surfaces.
3. The gripping surfaces should be defined by the opposite end portions of the blade itself in order to retain to the user the greatest possible tactile sensitivity to the degree of curvature in the blade and to the reaction of tissue to the cutting motion of the blade.
4. The gripping surfaces should be smoothly configured to avoid cutting or otherwise penetrating protective gloves worn by the user; and, these surfaces should provide handle means which aid the user in maintaining a secure grasp on the blade at points remote from any active cutting edge.
5. The flexibility of the blade should be established by design and should be selectable over a substantial range to suit individual users in a variety of applications.
6. The blade surface should be flat and smooth for ease of sterilization and packaging.
7. The manufacturing cost of the blade should be about the same as a standard razor blade in order that a blade, once used, may be disposed of without concern as to replacement cost.

Some of the shortcomings of a standard razor blade when used as a transverse excision device are identified and addressed by the disclosure of U.S. Pat. No. 4,943,295 issued to Hartlaub on Jul. 24, 1990. Rather than proposing a novel blade specifically designed to correct such shortcomings, Hartlaub discloses a standard double edged razor blade having fairly thick, molded finger grips that are bonded to and encase its opposite end portions. Another sheath-like guard made of flexible plastic or rubber extends longitudinally between the finger grips and receives that sharpened blade edge not then being used for cutting. By enclosing the opposite ends and the unused edge of a razor blade in specially configured protective structures attached to the blade, Hartlaub has indeed reduced the opportunities for inadvertent contact with dangerous edges and corners. It will, however, be appreciated that Hartlaub's attempt to cure the many problems attributable to the misapplication of a razor blade as a flexible surgical tool by encasing the blade edges with his grips and sheath fails to meet the detailed criteria listed above and discussed further hereinbelow.

SUMMARY OF THE INVENTION

A general object of this invention is to provide a flexible surgical blade which overcomes the aforementioned shortcomings of prior art devices and which meets the previously listed criteria of dermatologists and other blade users.

Another general object is to provide a blade of the type under consideration which has been particularly designed as a surgical implement and is essentially for tangential cutting of flat and protuberant skin lesions.

A specific object of this invention is to provide a thin, flexible cutting blade which may be gripped at its ends by a user's fingers for longitudinal flexing without concern that the fingers may slip and contact the sharpened longitudinal edge or edges of the blade.

Another specific object is to reduce the risks of cutting or puncturing the user's gloves and underlying skin without covering the ends or edges of the blade and thereby dulling the user's direct feel for the blade's condition and performance.

A more specific object of this invention is to provide a blade having a sharpened cutting edge formed along its longitudinal margin but extending less than the full blade length and intersecting with terminal protrusions integrally formed adjacent the blade ends and projecting transversely of the blade beyond its cutting edge. Such protrusions define generally semicircular extensions or bumpers which effectively recess the cutting edge and substantially shield the same from accidental contact by fingers gripping the ends of the blade.

Still another purpose of this invention is to provide a blade having a dog-bone shape wherein enlarged ends of the blade are provided with curved, finger receiving recesses and the intermediate shaft of the blade has a thickness that is somewhat less than that of the ends. It is contemplated that the transverse and longitudinal dimensions of the shaft may be selected to vary the flexibility of the blade.

Yet another object is to disclose several possible blade constructions which consistantly reflect these general parameters, namely:

1. The blade comprises a flexible, one-piece, flat body;
2. The ends of the blade project from the body to shield the blade's cutting edge or edges;
3. The blade ends provide safe and efficient finger grips; and,
4. The cutting edges of the blade extend over less than the full length of the leading edge of the blade.

A still more detailed object is to provide a blade having the above described characteristics which can be fabricated from flat, thin stock then heat treated and sharpened in a manner very similar to that used to produce commercial razor blades and at substantially the same cost. It is believed that the costs to produce, sterilize and package a flat, all metal surgical blade configured in accordance with this invention would be less than those required by the afore-described Hartlaub device, for example.

These and other advantages and objects of this invention and the manner of obtaining them will become apparent and the invention will be best appreciated and fully understood by having reference to the following detailed description of the embodiments of the invention taken in conjunction with the accompanying drawings.

DETAILED DESCRIPTION OF THE INVENTION

Figure 1:
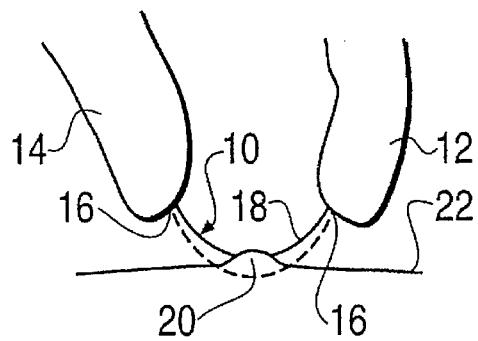
FIG. 1 is a frontal view of a flexed blade positioned relative to a skin protuberance for tangentially leveling or excising the same.

Referring to the drawings, FIG. 1 shows a surgical cutting blade, indicated generally by numeral 10, which may be utilized for removing skin lesions of both the protuberant and the flat types. The user's gloved finger 12 and thumb 14 grip the marginal ends 16 of the flexible blade thereby compressing the ends toward one another and forcing the central body portion 18 of the blade to bend convexly outwardly from the fingertips in a bow shape. The degree of flexure of the blade, hence its outward extend from the fingertips and the shape of the bow, can be maintained or selectively varied by a skilled user by digital pressure carefully applied to the blade ends. Although protective gloves are worn by the user, his sense of the reactive spring force of the blade and resistance of the blade to forward cutting movement provide tactile feedback enabling him to regulate closely the blade's shape and the muscular force required to advance the blade. In FIG. 1, the full line showing of blade 10 illustrates a degree of blade flexure suitable for leveling a protuberance 20 at or near the skin surface 22 while the broken line shows the blade 10 compressed sufficiently to undercut a saucer-shaped mass of the dermis underlying a flat lesion. A practiced blade user can control the depth of such undercutting and the size and shape of the excised tissue mass with great precision.

As indicated above in the background statement, the blade employed by most dermatologists comprises a standard razor blade 30 shown in FIG. 2 (a). This thin flat blade has sharpened edges 32 which are coextensive with the leading edges of the blade and which terminate in keen corners 34 proximate the blade end surfaces 36. The end surfaces are quite thin, usually on the order of four one thousands of an inch or less, and define projecting corners 38 which can cut or puncture a user's glove and underlying skin when the blade ends are grasped and compressed in the manner and for the purpose shown in FIG. 1. The risk of cutting through a protective glove when squeezing the blade edges just with a minimum of force required for correct blade flexure are apparent. The hazards presented by sharp edges 32 and corner 34 and 38 are ever present; and, injury is usually unavoidable should the user's fingers slip with respect to the flat end surfaces 36 of the blade 30.

Figure 2A:
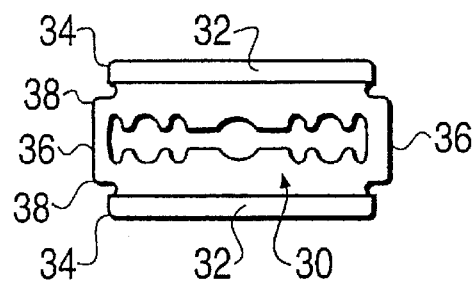
FIGS. 2 (a)–(d) are views illustrative of four prior art devices, respectively, pertinent to an understanding of this invention.
Figure 2B:
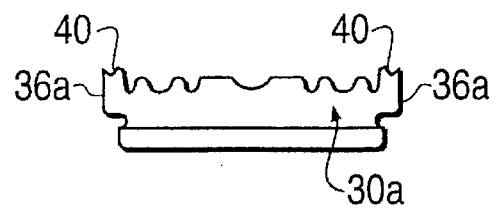

In order to reduce the stiffness of the standard razor blade 30, some users break the blade in two halves along its centerline in the manner shown in FIG. 2(b), to form a blade half 30a. The resulting blade half 30a is even more difficult to grip without cutting or penetrating the user's glove since the bearing surfaces 36a are only about half that of end surfaces 36. Moreover, digital contact with jagged corners 40 remaining along the broken edge of the half blade 30a are practically unavoidable as the surfaces 36a are squeezed toward one another. Thus it is seen that a desirable increase in the flexibility of blade 30 is accomplished at the expense of an even higher risk of inadvertent injury to the blade user.

Figure 2C:
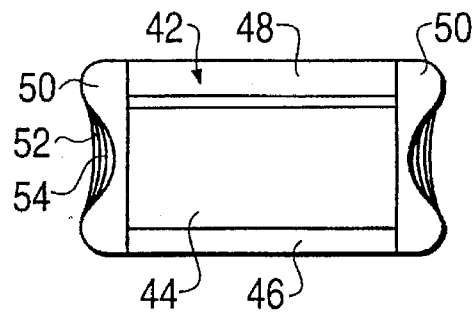

The surgical cutting tool shown in FIG. 2(c) and indicated in its entirety by numeral 42 is fully described in U.S. Pat.

No. 4,943,295 issued to Hartlaub who generally provides protective structural additions to a double-edged razor blade 44 having parallel sharpened edges extending the full length of the blade. One sharpened edge is shown at numeral 46 while the other is covered completely by a flexible sheath 48. Molded finger grips 50 are permanently attached to the opposite ends of the blade 44 and enclose the same to provide a protective cover for dangerous blade surfaces corresponding with surfaces 34, 36 and 38 of the aforedescribed blade 30. The outwardly facing thick surfaces of the grips provide rounded notches 52 and surface ridges 54 to enhance the user's grasp of the blade 42. The aforementioned sheath 48 has a longitudinal slot opening to its inner edge to receive therein a sharpened blade edge 46, not shown.

With the three auxilliary structures in place, i.e. ends 50 and sheath 48, the user's exposure to accidental injury is obviously reduced, but only with the added costs of fabricating and installing the protective structures. Since the type of blade under discussion can be expected to be contaminated with a patient's blood and in view of the current high concern with the exchange of blood between those who may be purposely or accidentally cut or scraped by the same blade, these blades are routinely discarded after initial use. Accordingly, increased costs associated with any type of protective means intended for attachment to a basic blade structure may increase the overall blade cost to an unacceptably high level.

Figure 3:
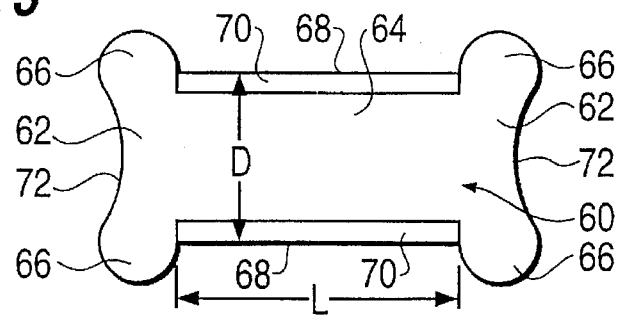
FIG. 3 is a top plan view of a blade according to this invention having the shaft dimensions of a dog-bone configuration indicated by the letters D and L.

Turning now to the preferred embodiments of the present invention, FIG. 3 depicts a blade 60 which is fabricated from thin, flat metal having suitable flexibility and resilience for its intended purpose. In outline the blade resembles a dog-bone in that it has enlarged ends 62 connected by an intermediate shaft 64. The ends 62 have generally semicircular lobes 66 extending transversly beyond the opposed longitudinal margins 68 of the shaft 64. Commencing at the inner edges of the lobes 66 and extending completely along the margins 68 between the lobes are formed parallel cutting edges 70 which have been honed or otherwise sharpened in a manner similar to that used to form a keen edge on a razor blade. Connecting the oppositely extending pairs of lobes 66 at each end of the blade 60 are reentrant curved surfaces 72 which are configured to conform generally to the size and shape of the thumb and finger surfaces which operatively engage the blade ends 62 in the fashion depicted in FIG. 1.

The letters D and L shown in FIG. 3 indicate the length and width of the shaft 64. To avoid the hazards discussed above which result from user's breaking a standard blade to increase blade flexibility, this invention contemplates that the shaft dimensions be selectable over a broad range to provide in a given blade that degree of flexibility best suited for a particular use and user. If, for example D is decreased while L is held constant, blade flexibility will increase and the cutting edge 70 will be more deeply recessed between the lobes 66. If D is held constant and L is decreased, the blade will become stiffer and the effective length of the cutting edge will decrease.

Figure 4:
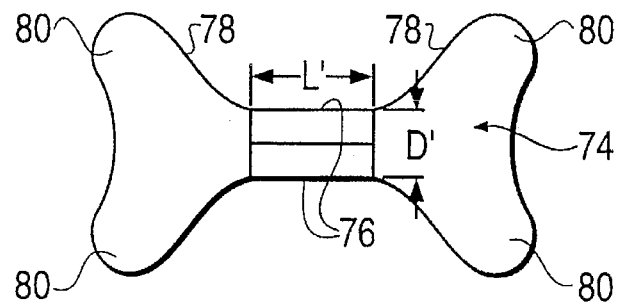
FIG. 4 is a top plan view similar to FIG. 3 wherein the indicated dimensions D' and L' have been substantially altered; and, FIGS. 5, 6 and 7 are top plan views of alternate embodiments which are, however, reflective of the same design parameters as the blades shown in FIGS. 3 and 4.

FIG. 4 shows a blade 74 similar to that shown in FIG. 3 where D' has been reduced to such an extent that the opposed cutting edges 76 are contiguous. The illustrated cutting edge length L' has been shortened to such an extent that curved transitional edges 78 are required to connect smoothly the lobes 80 and the cutting edges 76. From a consideration of the structural variables shown in FIGS. 3 and 4, it will be appreciated that innumerable variations of cutting edge length and shaft flexibility are available while retaining the desirable dog-bone shape of the blade.

Figure 5:
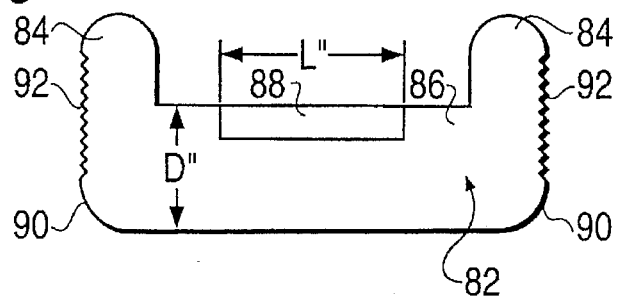

FIG. 5 depicts a single-edged blade 82 having frontally extending semicircular lobes 84. The width of the blade body 86 indicated by D" has been selected to recess the cutting edge 88 considerably rearwardly of the leading edges of the lobes 84. The cutting edge 88 has an indicated length L" which may be made longer or shorter as desired. It will be appreciated that either of the earlier described blades 60 and 74 and the hereinafter described blade 104 may be provided but a single edge in the interest of reducing manufacturing costs. The blade 82 does not have ends provided with curved finger grips like that shown at 72 in FIG. 3. Instead this embodiment has parallel end edges 90 which are serrated, such as finely notched edges, to define projections at 92 to grip, but not abrade or puncture, protective gloves.

Figure 6:
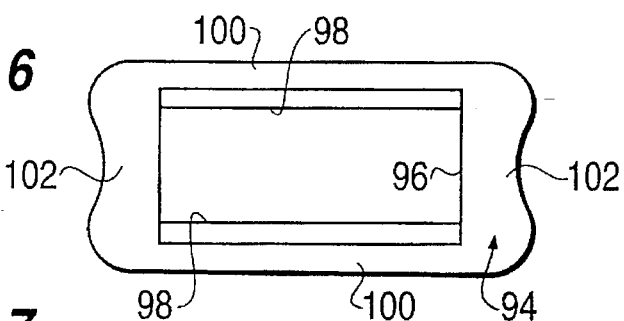

FIG. 6 shows another blade embodiment 94 which has a central rectangular opening 96 defining longitudinally extending marginal edges 98 which face inwardly toward one another. The edges 98 are sharpened appropriately and are nicely shielded from accidental finger contact by the spaced, parallel body portions 100 which connect the blade end portions 102. The dimensions of the opening 96 will determine the flexibility of a blade body of given width and length. The blade end surfaces 102 are provided with curved finger grips like those shown at 72 in FIG. 3.

Figure 7:
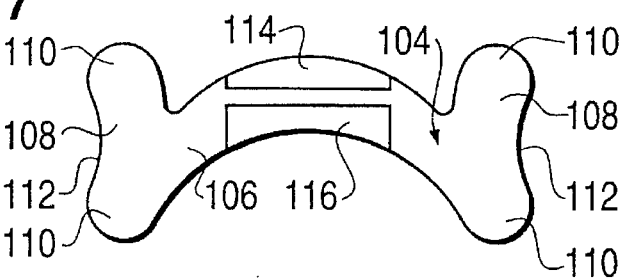

FIG. 7 depicts a blade 104 which is similar to the dog-bone shaped blades illustrated in FIGS. 3 and 4 except that the shaft 106 connecting the blade ends 108 is curved. The blade ends carry projecting lobes 110 which are connected by curved finger grips 112. The shaft 106 may have one or both of the sharpened edges 114 and 116, as desired. The blade shaft 106 is curved as shown to facilitate the excision of proturberances from certain body surfaces which can be conveniently addressed only by a cutting surface 114 that projects forwardly somewhat ahead of the user's fingers.

The blades described above are intended to effect tangential excision of skin lesions in essentially the same manner as do the common razor blades 10 and 30 depicted in FIGS. 1 and 2(a)–(c), respectively. However, a clear-cut advantage of this invention over known prior art becomes palpable to professional users of such blades when a very important secondary aspect of blade performance is considered, namely, the elimination or reduction of the dual hazards of trauma and infection for blade users and patients. In accordance with this invention, this important aspect is achieved by a blade construction which incorporates all of the structural parameters enumerated above in the Summary of the Invention whereby the several essential blade criteria enumerated under the Background Of The Invention can be achieved.

Applying these parameters and criteria to the first-described embodiment shown in FIG. 3, it will be seen that the blade 60 is a flexible flat body formed in one piece. The projecting lobes 66 comprising part of the ends 62 of the blade shield the cutting edges 70 by effectively recessing the same into the blade body and by providing protruding guards or bumpers which block inadvertant slippage of a user's finger around the ends of the blade. The blade ends provide long smooth edges free of any sharp surfaces such as those carried by the standard blade 30 at 34 and 38. The efficiency of the blade ends 62 as grips is enhanced by the curved recesses 72 and the lateral projection of the lobes 66 which tend to position and retain the grasping digits properly. Finally, the ends of the cutting edges 70 are not exposed at the end surfaces of blade 60 as the cutting edges 32 of blade 30 are exposed to contact by a finger pressing on end surface 36. Instead, the cutting edges of blade 60 are physically isolated from the end surfaces 72 by the intervening, projection lobes 66.

Having been constructed in accordance with the above-enumerated parameters, it will be seen that the blade 60 meets or exceeds all of the desirable blade features. Thus, the shank 64 of the blade is flexible and its flexibility can be substantially varied by adjusting the dimensions D and L. The gripping fingers of the user are well protected from the blade's only sharp surfaces 70 by the combined action of the blade shielding lobes 66 and the finger grips which are spaced from the blade surfaces 70 and defined by the arcuate recesses 72 at the blade ends 62. The surface of the blade 60 is flat and free from any recesses or surface protuberances which might complicate its sterilization or packaging. And, finally, the cost to manufacture blade 60, including the initial tooling cost, should not be substantially greater than that associated with a commercial razor blade assuming that comparable numbers of blades are produced.

While only blade 60 has been considered in detail with regard to its ability to meet the several specific criteria set forth herein, it will be appreciated that the common structural features observable among all the blade embodiments shown and described herein enable each of these blades to meet the stated criteria.

Figure 2D:
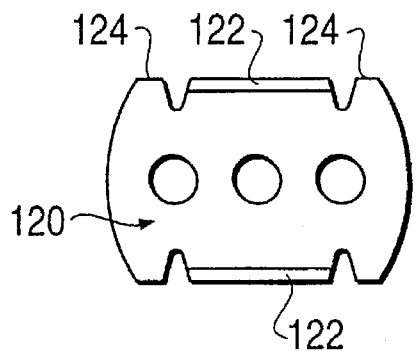

The lowermost blade 120 shown in FIG. 2(d) is a patented prior art device and may be thought to be somewhat pertinent to this invention because it depicts cutting edges 122 which do not extend the full length of the leading edge of the blade. However, a careful reading of the complete specification of U.S. Pat. No. 2,041,778 issued to Peters on May 26, 1936, indicates that nothing more than partial sharpening of the leading blade edge is diclosed and the spaced end segments 124 of the edges do not extend beyond the leading edge 122 to protectively recess the sharpened portion 122 therebetween. Clearly, several other essential structural features needed to meet the criteria set forth to this disclosure are not taught or suggested by the Peter's patent.

The foregoing description of the embodiments of the invention shown in the drawings is illustrative and explanatory only; and, various changes in size, shape and materials, as well as in specific details of the illustrated construction may be made without departing from the scope of the invention. Therefore, I do not intend to be limited to the details shown and described herein, but intend to cover all changes and modifications which are encompassed by the scope and spirit of the appended claims.

What I claim as my invention is:

1. A unitary flexible blade body having a cutting edge formed between opposed end margins and along at least a portion of at least one of two longitudinal margins of said body; the end margins of said body defining projecting portions located proximate to said blade body extending longitudinally beyond said cutting edge and transversely beyond at least the one frontal longitudinal margin having said cutting edge, said cutting edge recessed between said projecting portions, said projecting portions providing digital grippers having a non-slip digital engagement surface suitable for longitudinal flexing of said cutting edge by a user and protruding guards to preclude inadvertent slippage of a user's digit from around the end margins to said cutting edge of said blade body.

2. The blade body defined in claim 1, wherein: said cutting edge terminates at said projecting portions.

3. The blade body defined in claim 2, wherein: said cutting edge defines a curved surface.

4. The blade body defined in claim 1, wherein: said non-slip digital engagement surface of said digital grippers define a plurality of projections disposed generally along a longitudinal axis of said blade body to facilitate digital gripping thereof.

5. The blade body defined in claim 1, wherein said non-slip digital engagement surface of said digital grippers of the end margins of said body having a concave surface; said projecting portions defining frontal margins having a semicircular surface; said end margins and said frontal margins jointly forming said digital grippers having a concave surface.

6. The blade body defined in claim 5, wherein: said projecting portions define semi-circular lobes extending transversely beyond at least one of said longitudinal margins of said cutting edge portion of said blade body to form said protruding guards.

7. The blade body defined in claim 1, wherein: said longitudinal margin of said blade body is in part defined by an opening through said blade body.

8. A unitary flexible blade body having a cutting edge formed along at least a portion of at least one of two longitudinal margins of said body; said body having opposed end margins defining projecting portions located proximate to said blade body extending longitudinally beyond said cutting edge and transversely beyond both longitudinal margins, said cutting edge recessed between said projecting portions, said projecting portions providing digital grippers having a non-slip digital engagement surface suitable for longitudinal flexing of said cutting edge by a user and protruding guards to preclude inadvertent slippage of a user's digit from around the end margins to said cutting edge of said blade body.

9. The blade body defined in claim 8, wherein: said longitudinal margin having said cutting edge portion defining a flexible longitudinal shaft terminating at opposite ends by said protruding guards of said projecting portions.

10. The blade body defined in claim 9, wherein: said flexible longitudinal shaft defines said cutting edge to be curved along said longitudinal margin of said blade body.

11. The blade body defined in claim 9, wherein: said protruding guards include oppositely extending semicircular lobes spaced by a concave surface forming said non-slip digital engagement surface of said digital grippers.

12. A flexible blade body including a planar blade portion having a cutting edge formed between opposed end margins of said blade body and along at least a portion of at least one of two longitudinal margins of said body; the end margins of said body defining projecting portions located proximate to said blade body extending longitudinally beyond said cutting edge and transversely beyond at least the one frontal longitudinal margin having said cutting edge, said cutting edge recessed between said projecting portions, said projecting portions providing digital grippers having a non-slip digital engagement surface defining a plurality of projections disposed generally along a longitudinal axis of said blade body, said digital grippers suitable for longitudinal flexing of said cutting edge by a user to preclude inadvertent slippage of a user's digit to said cutting edge of said blade body.

13. The blade body of claim 12, wherein said plurality of projections disposed generally along a longitudinal axis of said blade body define said non-slip gripping surface.

14. The blade body of claim 13, wherein said projections define a serrated gripping surface.

* * * * *